United States Patent
Baeke

(10) Patent No.: US 11,806,222 B2
(45) Date of Patent: Nov. 7, 2023

(54) APPARATUS FOR CUTTING A MATERIAL AND A METHOD FOR CUTTING A NEGATIVE PRESSURE WOUND THERAPY DRESSING

(71) Applicant: John Baeke, Boerne, TX (US)

(72) Inventor: John Baeke, Boerne, TX (US)

( * ) Notice: Subject to any disclaimer, the term of this patent is extended or adjusted under 35 U.S.C. 154(b) by 183 days.

(21) Appl. No.: 17/444,593

(22) Filed: Aug. 6, 2021

(65) Prior Publication Data
US 2023/0045643 A1   Feb. 9, 2023

(51) Int. Cl.
*A61F 15/02* (2006.01)
*A61F 13/00* (2006.01)
*A61F 13/02* (2006.01)
*A61F 13/15* (2006.01)
*A61M 1/00* (2006.01)

(52) U.S. Cl.
CPC ........ *A61F 15/02* (2013.01); *A61F 13/00068* (2013.01); *A61F 13/0276* (2013.01); *A61M 1/91* (2021.05); *A61F 2013/15073* (2013.01)

(58) Field of Classification Search
CPC ............ A61F 13/0276; A61F 13/00068; A61F 15/02; A61M 1/91
See application file for complete search history.

(56) References Cited

U.S. PATENT DOCUMENTS

| | | | | | |
|---|---|---|---|---|---|
| 2,145,725 | A | * | 1/1939 | Jamieson | B26F 1/3846 30/360 |
| 2,708,312 | A | * | 5/1955 | Hauser | A21C 11/106 30/178 |
| 3,683,499 | A | * | 8/1972 | Robinson, Jr. | B21D 28/343 30/360 |
| 3,984,041 | A | * | 10/1976 | LePage | A41H 37/006 D8/52 |

(Continued)

FOREIGN PATENT DOCUMENTS

WO    2019199596 A1   10/2019

OTHER PUBLICATIONS

NPWT Training—How to apply dressing for negative pressure wound therapy https://www.youtube.com/watch?v=-0eeoacEw-k (Year: 2019).*

(Continued)

*Primary Examiner* — Sean M Michalski
(74) *Attorney, Agent, or Firm* — INNOVATION CAPITAL LAW GROUP, LLP; Vic Lin

(57) ABSTRACT

A method for accurately, rapidly and consistently cutting an opening in drape material for negative pressure wound therapy (NPWT) uses a cutting device that includes a plurality of cutting members that can extend from a bottom surface of the cutting device. A cover may fit over the bottom to protect the cutting members. The cutting members may be positioned to define a cut-out shape having dimensions designed for use with a NPWT system. An adhesive material (Continued)

may be formed on the bottom surface of the cutting device, inside of the cut-out shape defined by the cutting members. In use, the user presses the cutting tool onto the drape to cause the cutting members to cut into the drape and the adhesive to stick to the drape. When the user lifts the device, the drape, cut to the correct size and shape, is removed from the foam dressing covering the wound.

15 Claims, 7 Drawing Sheets

(56) References Cited

U.S. PATENT DOCUMENTS

| | | | | |
|---|---|---|---|---|
| 4,087,913 | A * | 5/1978 | Jackson | B28D 1/041 30/360 |
| 4,753,010 | A * | 6/1988 | Franovich | A61B 17/32053 30/316 |
| 4,974,462 | A * | 12/1990 | Rising | B01D 29/01 73/864.41 |
| 5,071,428 | A * | 12/1991 | Chin | A61N 1/0587 81/418 |
| 5,146,794 | A * | 9/1992 | Rising | B01D 29/01 73/864.41 |
| 5,361,664 | A * | 11/1994 | Desmarais | B26F 1/3846 83/633 |
| 6,009,625 | A * | 1/2000 | Keathley | B26F 1/0015 30/316 |
| 7,011,009 | B1 * | 3/2006 | Tomich | B26F 1/02 83/698.21 |
| 7,228,776 | B2 * | 6/2007 | Case | B21D 28/343 408/233 |
| 7,424,780 | B2 * | 9/2008 | Cicchitti | B26F 1/3846 30/310 |
| 7,790,946 | B2 | 9/2010 | Mulligan | |
| 8,740,970 | B2 * | 6/2014 | Hamman | A61B 17/0293 623/1.36 |
| 8,758,328 | B2 | 6/2014 | Locke et al. | |
| 9,878,077 | B2 | 1/2018 | Locke et al. | |
| 10,576,189 | B2 | 3/2020 | Locke et al. | |
| D886,648 | S | 6/2020 | Carroll et al. | |
| 11,000,282 | B2 * | 5/2021 | Schuelke | A61B 17/32002 |
| 2002/0166425 | A1 | 11/2002 | Takeuchi et al. | |
| 2003/0078610 | A1 * | 4/2003 | Yedlowski | A61F 13/046 606/179 |
| 2003/0171811 | A1 * | 9/2003 | Steiner | A61L 27/386 623/13.17 |
| 2004/0243073 | A1 * | 12/2004 | Lockwood | A61F 17/00 602/41 |
| 2006/0161193 | A1 * | 7/2006 | Beane | A61F 2/06 606/185 |
| 2007/0260207 | A1 | 11/2007 | Ugander et al. | |
| 2007/0293830 | A1 | 12/2007 | Martin | |
| 2008/0287892 | A1 * | 11/2008 | Khan | A61M 1/985 604/289 |
| 2010/0036333 | A1 * | 2/2010 | Schenk, III | A61M 1/982 604/313 |
| 2010/0160916 | A1 * | 6/2010 | Chana | A61B 17/175 606/83 |
| 2010/0168871 | A1 * | 7/2010 | Liao | A61F 2/2875 623/23.72 |
| 2010/0256545 | A1 * | 10/2010 | Aali | A61F 13/00063 604/304 |
| 2011/0213287 | A1 * | 9/2011 | Lattimore | A61F 13/00017 604/319 |
| 2012/0271336 | A1 * | 10/2012 | Hamman | A61B 17/0293 606/186 |
| 2013/0261575 | A1 * | 10/2013 | Kiyoshi | A61B 5/1075 156/64 |
| 2015/0159066 | A1 * | 6/2015 | Hartwell | A61F 13/0216 604/319 |
| 2016/0120706 | A1 * | 5/2016 | Collinson | A61M 1/913 604/319 |
| 2016/0144084 | A1 * | 5/2016 | Collinson | A61L 15/42 604/319 |
| 2016/0325028 | A1 * | 11/2016 | Locke | A61M 1/85 |
| 2018/0177642 | A1 * | 6/2018 | Anderson | A61F 13/04 |
| 2019/0029705 | A1 | 1/2019 | Vardi et al. | |
| 2020/0030153 | A1 * | 1/2020 | Johannison | A61L 24/046 |
| 2020/0155736 | A1 | 5/2020 | Locke et al. | |
| 2021/0000496 | A1 * | 1/2021 | Herrin | A61B 17/32002 |
| 2021/0161721 | A1 * | 6/2021 | Carroll | A61F 13/00068 |
| 2021/0259890 | A1 * | 8/2021 | Carty | A61L 15/28 |
| 2022/0211932 | A1 * | 7/2022 | Robinson | A61F 13/0276 |
| 2022/0287884 | A1 * | 9/2022 | Kharkar | A61F 13/0216 |
| 2022/0288297 | A1 * | 9/2022 | Carroll | A61F 13/0216 |
| 2022/0370254 | A1 * | 11/2022 | Seddon | A61F 15/02 |
| 2023/0045643 | A1 * | 2/2023 | Baeke | A61M 1/91 |

OTHER PUBLICATIONS

International Search Report & Written Opinion dated Oct. 7, 2022 from PCT Application No. PCT/US22/73472.
International Preliminary Report on Patentability (Chapter II) dated Aug. 17, 2023 from PCT Application No. PCT/US2022/073472.
NPWT Training How to Apply Dressing for negative pressure wound therapy; https://www.youtube.com/watch?v=-0eeoacEw-k.

* cited by examiner

APPARATUS FOR CUTTING A MATERIAL AND A METHOD FOR CUTTING A NEGATIVE PRESSURE WOUND THERAPY DRESSING

BACKGROUND OF THE INVENTION

1. Field of the Invention

Embodiments of the invention relate generally to devices for cutting a material and methods for using the same. More particularly, embodiments of the invention relate to a method and device for rapidly and precisely cutting an opening in any negative pressure wound therapy (NPWT) dressing drape.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

It is known that that wounds heal more quickly when subjected to negative pressure, such as suction of vacuum. Thus, a special wound dressing was designed which delivers suction directly to the wound. This dressing requires an air-tight seal, otherwise any leak would destroy the vacuum.

Referring to FIG. 7, a vacuum assisted closure system includes a pump 40 that can have a suction tube 42 extending therefrom. A special foam dressing 44 can be applied to the wound 48. Typically the dressing 44 is applied directly to the wound 48 and is sized to closely match the size of the wound 48. Over the foam dressing 44 is placed a drape 46 that is larger than the foam dressing 44 so that it completely frames the foam dressing 44 and adheres to the normal surrounding skin, thus providing a seal. The drape 46 typically has a peel-back temporary cover that can be removed exposing an adhesive surface to adhere the drape 46 to the foam dressing 44 and the user's skin.

The suction tube 42 can deliver vacuum to the wound 48. At the distal end of the suction tube 42 is typically one or two round discs 50 which can also include a peel-back adhesive on a portion of its bottom surface. This can connect the suction tube 42 on the top of drape 46, providing another air-tight seal.

Healthcare providers are using various homemade devices and clumsy techniques to create the requisite round opening in the adhesive drape 46 of various NPWT dressings. These practices usually result in drape openings too small or improperly shaped which, in turn, interfere with proper functioning of the NPWT equipment. Further, these same practices are clumsy and time-consuming; often utilize unclean, dull instruments and almost always damage the special foam dressing 44. With the drape 46 adhered to the foam dressing 44, it can be difficult for the healthcare provider to not only cut the drape 46 to the correct size, but to also then peel away the cut drape from the foam dressing. The healthcare provider can take considerable time to cut the properly sized and shaped hole in the drape without jabbing the patient's wound and without gouging the foam dressing. Improperly cut holes in the drape can interfere with the suction or could interfere with the transmission of information via small ports in the disc 50 that send information back to the system.

In view of the foregoing, there is a need for a tool for cutting a properly and consistently sized hole in a drape for vacuum assisted closure treatment; and do so expeditiously. In the operating theatre where the Negative Pressure Wound Therapy device is often utilized, surgical facility fees and anaesthesia services typically charge by the minute. On both the acute and extended care wards, nursing staff are commonly overworked. Any method to lessen their work burden increases the quality of care and healthcare costs for all.

SUMMARY OF THE INVENTION

Embodiments of the present invention provide a method for cutting a wound dressing material disposed on a patient comprising disposing a cutting tool on the wound dressing material; pressing the cutting tool onto the wound dressing material to cause cutting members extending from a bottom surface of a base member of the cutting tool to perforate the wound dressing; and lifting the cutting tool away from the patient with the wound dressing adhered to an adhesive surface disposed on the bottom surface of the base member.

Embodiments of the present invention further provide a method for cutting through a drape disposed over a foam dressing for treating a wound by negative pressure wound therapy comprising disposing a cutting tool on the drape; pressing the cutting tool onto the drape to cause cutting members extending from a bottom surface of a base member of the cutting tool to perforate the wound dressing without substantially damaging the foam dressing there below; and lifting the cutting tool away from the patient with the cut drape adhered to an adhesive surface disposed on the bottom surface of the base member, wherein the cutting members are disposed in a predefined shape and size along the bottom surface, the predefined shape and size matching a shape and size proscribed by a system for providing the negative pressure wound therapy.

Embodiments of the present invention also provide a method for treating a wound by negative pressure wound therapy comprising disposing a foam dressing over the wound; adhering an adhesive side of a drape to the foam dressing, the drape extending about an entire periphery of the foam dressing and adhering to skin of a patient; disposing a cutting tool on the drape; pressing the cutting tool onto the drape to cause cutting members extending from a bottom surface of a base member of the cutting tool to perforate the wound dressing without substantially damaging the foam dressing there below; lifting the cutting tool away from the patient with a cut portion of the drape adhered to an adhesive surface disposed on the bottom surface of the base member; attaching a suction disc to an opening formed by removal of the cut portion of the drape; and applying suction at a portion of a base of the suction disc to create a negative pressure at the wound.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Figure 1:
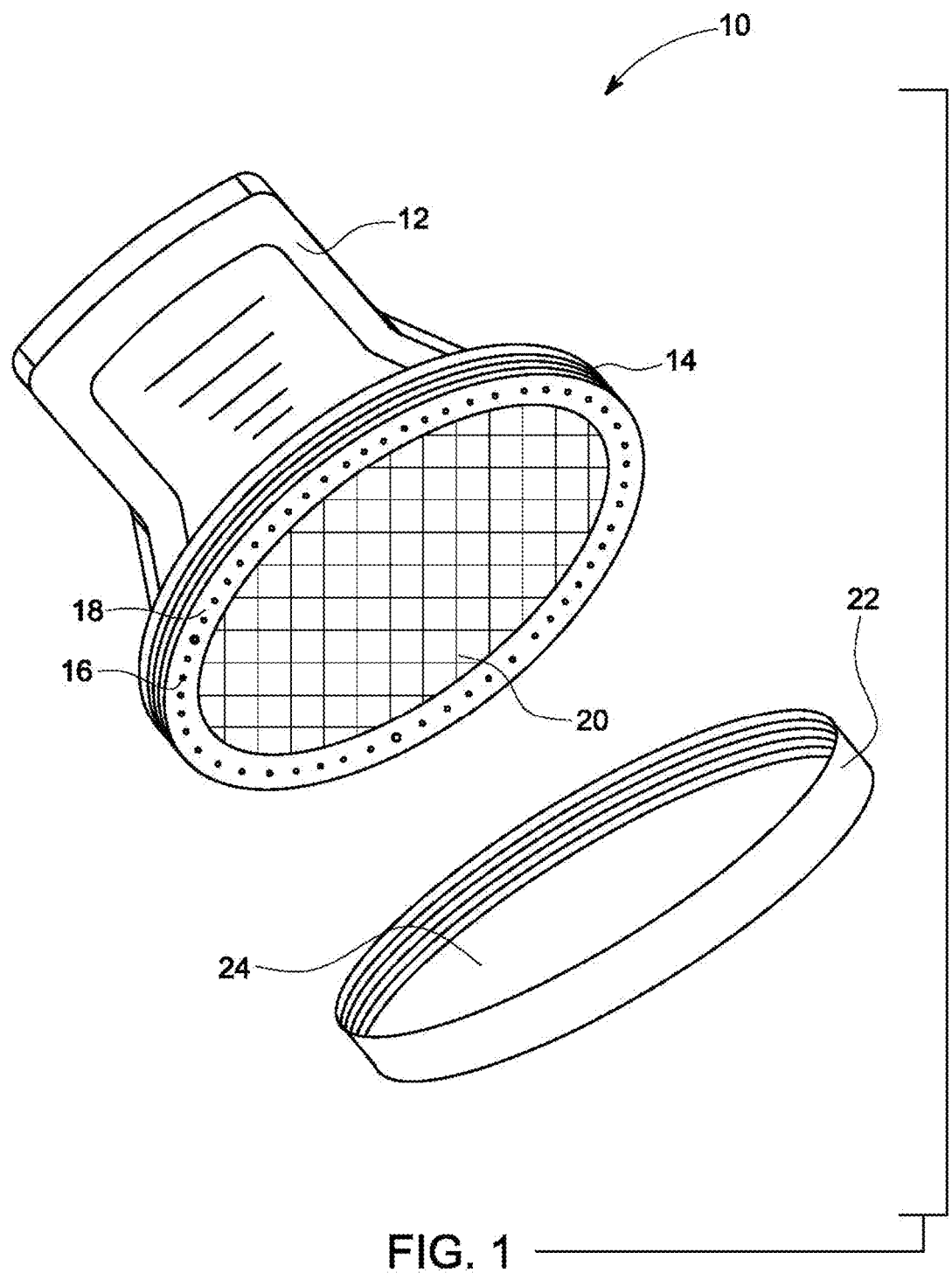
FIG. 1 illustrates perspective view of a tool for cutting a drape for negative pressure wound therapy, with cutting pins retracted, according to an exemplary embodiment of the present invention.

Unless otherwise indicated illustrations in the figures are not necessarily drawn to scale or proportion.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

As is well known to those skilled in the art, many careful considerations and compromises typically must be made when designing for the optimal configuration of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Broadly, embodiments of the present invention provide a method for accurately, rapidly and consistently cutting an opening in a drape material for delivery of negative pressure wound therapy. The cutting device can include a plurality of cutting members that can extend from a bottom surface of the cutting device. The cutting members may be pins, blades or the like. The cutting members may move between a retracted state to a deployed state, or the cutting members may be permanently configured in the deployed state and a cover may fit over the bottom to protect the cutting members. The cutting members may be spaced apart to provide a cut-out shape having dimensions suitable for use with a suction disc of a NPWT system. An adhesive material may be formed on the bottom surface of the cutting device 62, inside of the cut-out shape defined by the cutting members. In use, the user presses the cutting tool onto the drape 46 to cause the cutting members 34 to cut into the drape and the adhesive to stick to the drape. When the user lifts the device, a portion of the drape, cut to the correct size and shape, is removed from the foam dressing covering the wound.

Figure 2:
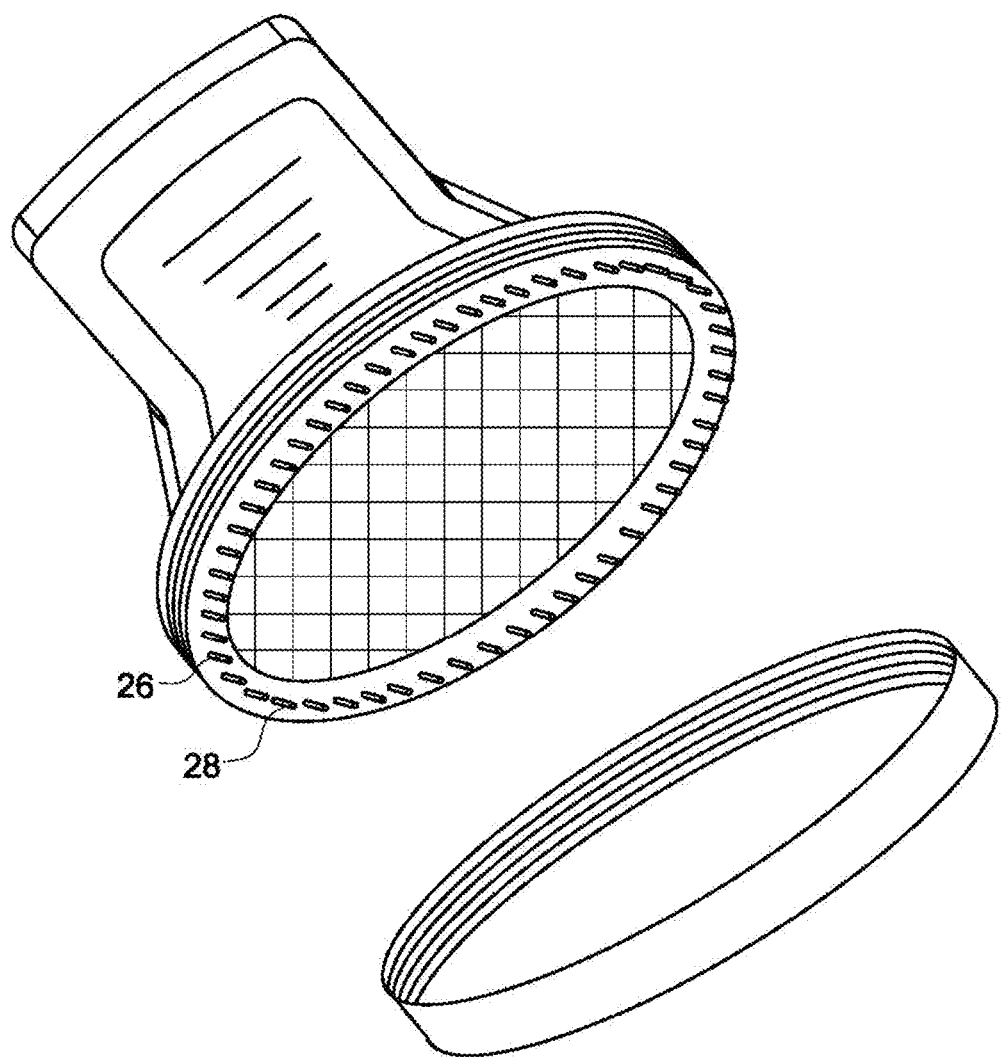
FIG. 2 illustrates perspective view of a tool for cutting a drape for negative pressure wound therapy, showing cutting pins deployed, either permanently, or temporarily from the retracted state of FIG. 1, according to an exemplary embodiment of the present invention.
Figure 3:
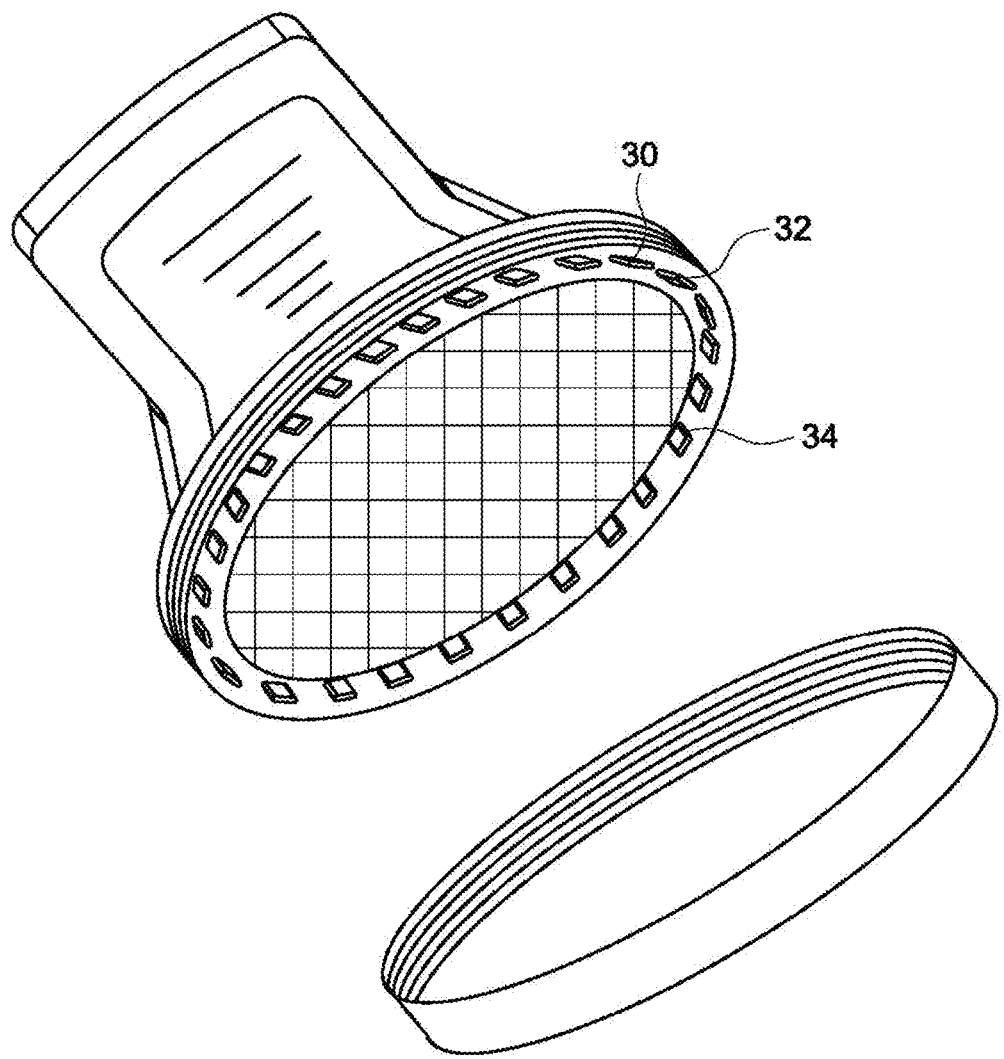
FIG. 3 illustrates perspective view of a tool for cutting a drape for negative pressure wound therapy, showing cutting blades deployed, either permanently, or temporarily from the retracted state, according to an exemplary embodiment of the present invention.
Figure 7:
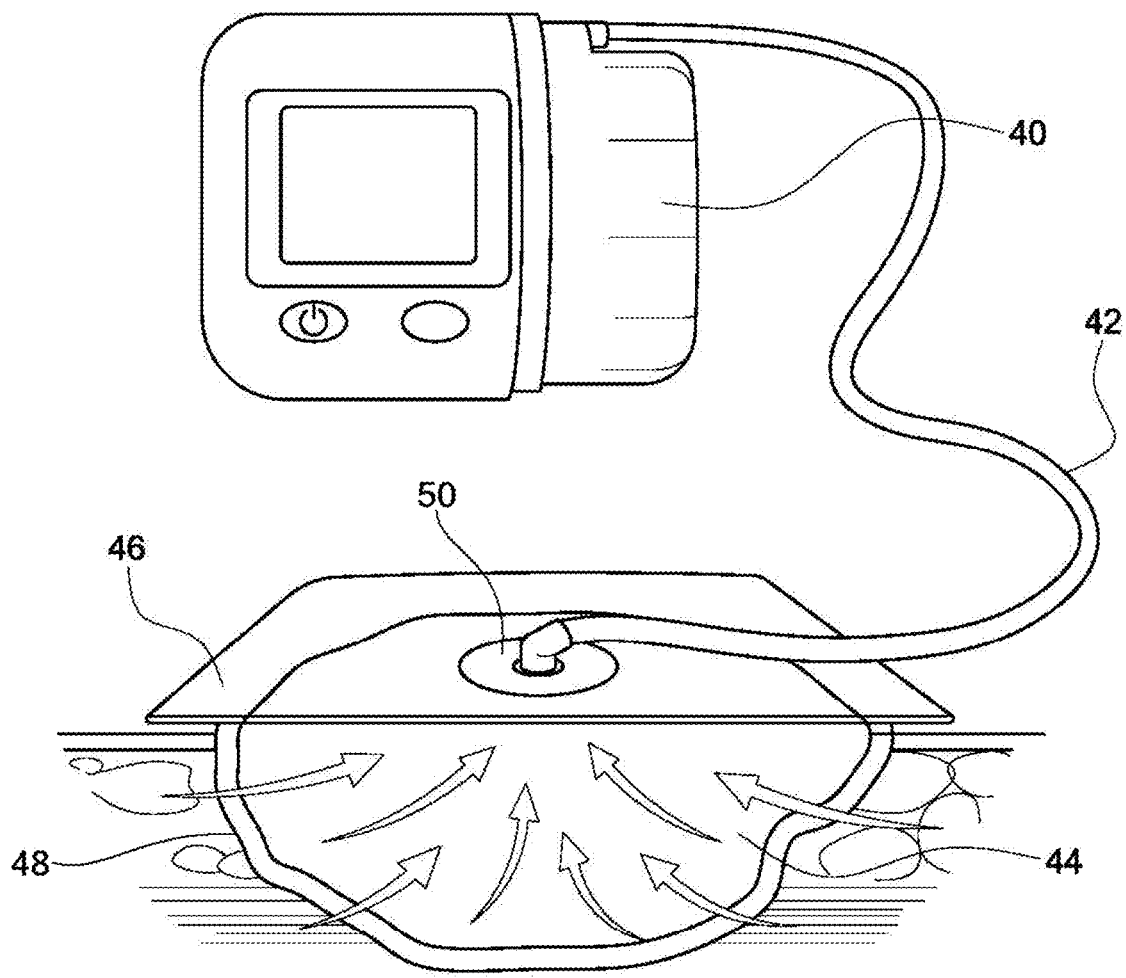
FIG. 7 illustrates a negative pressure wound therapy system connected to the opening of FIG. 6B.

Referring to FIGS. 1, 2 and 7, a cutting tool 10 can include a grip 12 extending from a back side of a base member 14. A plurality of cutting member openings 16 may be disposed about a bottom side 18 of the base member 14. The cutting member openings 16 may be arranged in a shape that is sized and shaped according to the requirements of a NPWT system, such as that shown in FIG. 7, for example. The shape may be a circle, as shown in FIGS. 1 through 3, or may be in any desired shape, depending on the specifications of the NPWT system.

An adhesive surface 20 may be formed inside of the shape defined by the cutting member openings 16 on the bottom side 18 of the cutting tool 10. A removable covering (not shown) may protect the adhesive surface 20 when the cutting tool 10 is not in use. Typically, the adhesive forming the adhesive surface 20 may be configured to adhere to the drape (such as drape 46 shown in FIG. 7) more strongly than the adhesive used to adhere the drape 46 to the foam dressing 44. Accordingly, when the adhesive surface 20 is applied to the drape 46 and the cutting tool 10 lifted off the wound dressing, the drape 46 will unadhere from the foam dressing 44.

A cover 22 may be used to cover the bottom side 18 of the cutting tool 10. The cover 22 may fit onto the cutting tool 10 in various manners. In some embodiments, as shown in FIGS. 1 through 3, an inside lip may include grooves and projections that can made with similar grooves and projections on the outer surface of the base member 14. Of course, other fits, such as a screw fit, a friction fit, or the like, may be used to store the cover 22 on the base member 14 to protect the bottom side 18 thereof.

As shown in FIG. 2, cutting pins 26 can extend out of the cutting member openings 16. The cutting pins 26 may include a sharpened tip 28 such that the cutting pins 26 can extend through the drape 46 when the cutting tool 10 is pressed onto wound dressing that includes the drape 46 covering a foam dressing 44 disposed over a wound 48. It should be understood that the length of the cutting pins 26 (as well as the cutting blades 30, discussed below with reference to FIG. 3) are not necessarily shown to scale. A length of the cutting pins 26 may be such that they cut into the drape 46 without substantially damaging the foam dressing 44 thereunder; or making contact with viable tissue. Substantial damage may be damage that renders the foam dressing unsuitable for its purpose. Such substantial damage may include gouging, deep cutting or separating portions of the foam dressing away from the remainder thereof. Thus, the cutting pins 26 can perforate the drape 46 while not significantly perforating the foam dressing 44 or by only pressing into the foam dressing such that any partial perforations do not change the operation of the negative pressure wound therapy system during use thereof.

Further, while the figures show a particular spacing between the cutting pins 26, such spacing may be configured so that, when the cutting tool 10 is lifted, the drape 46 is removed along the perforations formed by the cutting pins 26 without any tearing outside of the desired shape.

Figure 4:
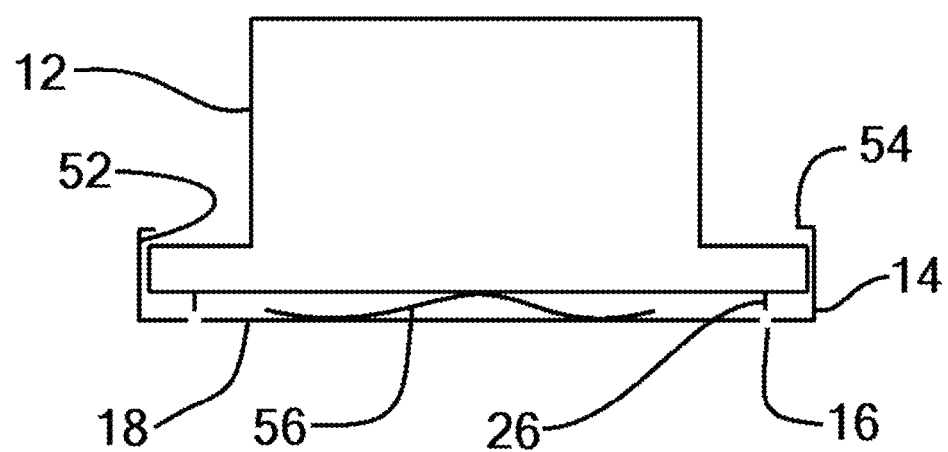
FIG. 4 illustrates a schematic representation of a side view cross-section of the cutting tool of FIG. 1, illustrating an optional retraction mechanism.

The cutting pins 26 may permanently extend from the base member 14, as shown in FIG. 2. In some embodiments, as schematically represented in FIG. 4, the cutting pins 26 may retractably extend from the cutting member openings 16. For example, the grip 12 may slide along the side wall interior 52 of the base member 14, where the cutting pins 26 are connected with the grip 12. A stop 54 can retain the base member 14 from sliding off the grip 12. A resilient member 56, such as a spring, may be used to keep the grip 12 (and thus, the cutting pins 26) in the retracted configuration (as shown in FIG. 4). When the user presses the cutting tool 10 onto the patient, the force of the user pressing down on the grip 12 can cause the cutting pins 26 to extend out of the cutting member openings 16 and perforate the drape 46. When the user lifts the cutting tool 10 off of the patient, the cutting pins 26 can retract back into the base member 14 with the drape 46 stuck to the adhesive surface 20. It should be understood that other retraction methods may be used to retract and deploy the cutting pins 26.

Referring to FIGS. 3 and 7, the cutting pins 26, discussed above, may be replaced by cutting blades 30. The cutting blades 30 may operate in a manner similar to the cutting pins 26. The cutting blades 30 may include a sharpened end surface 32 for perforating the drape 46 when pressed thereinto. In some embodiments, one or both side surfaces 34 may be sharpened, where a user may press the cutting tool with the cutting blades 30 into the drape 46 and then slightly twist the cutting tool to cause the sharpened side surfaces 34 to further cut the drape 46 completely into the desired shape.

The spacing between the cutting blades 30 may be such that the perforations provided are sufficient to cause the drape 46 to be removed from the foam dressing 44 when the cutting tool is lifted off the patient.

While generally rectangular blades are shown, other shapes may be used within the scope of the present invention. Further, as discussed above with respect to the cutting pins, the cutting blades 30 may have a suitable length for cutting through the drape 46 without significantly damaging or cutting the foam dressing 44.

Further, similar to the cutting pins, the cutting blades 30 may be permanently extending from the bottom surface 18 of the base member 14 (see FIG. 2) or may be retractably disposed in the cutting tool in a manner, for example, as described above with respect to FIG. 4.

Figure 5:
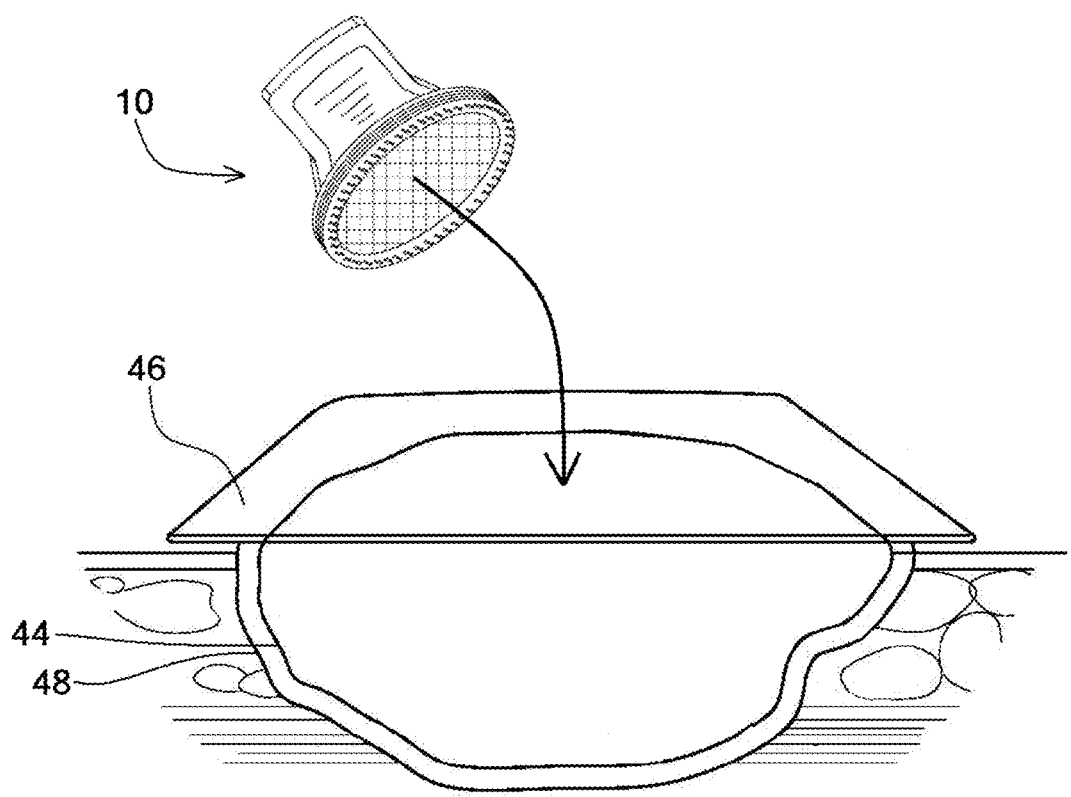
FIG. 5 illustrates application of the cutting device of FIG. 2 onto a wound site of a patient, according to an exemplary embodiment of the present invention.

FIG. 5 illustrates the application of the cutting device 10 of FIG. 2 onto a wound site of a patient, where the wound 48 is covered with the foam dressing 44 and the foam dressing 44 is covered by the drape 46, with the drape extending over and adhered to the patient's skin.

Figure 6A:
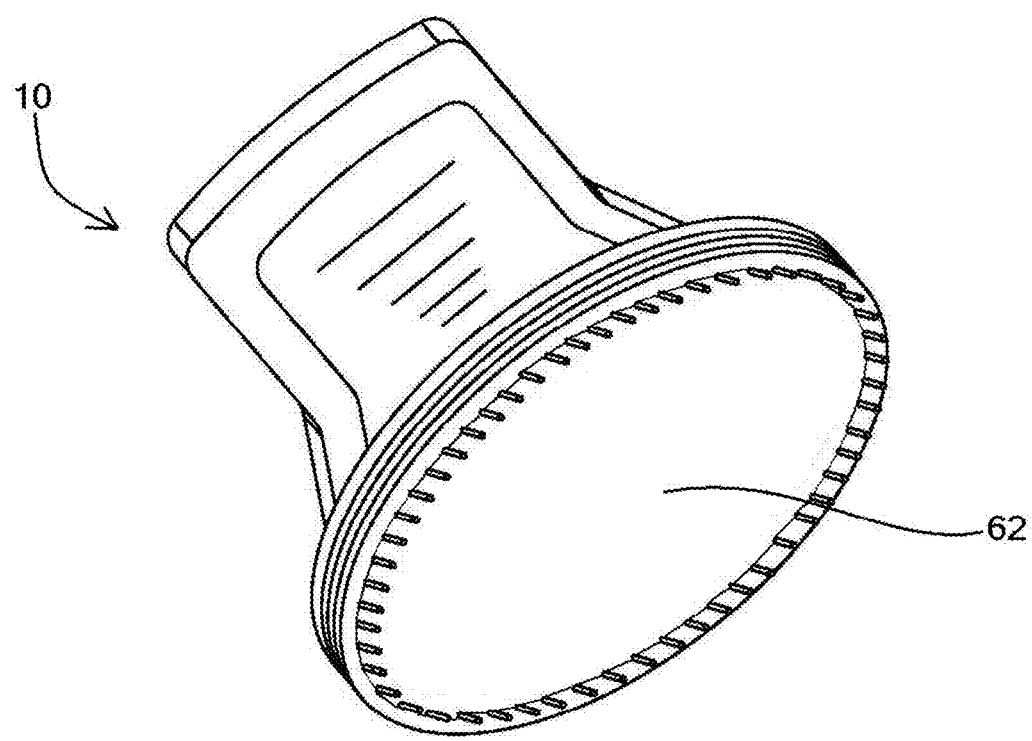
FIG. 6A illustrates the cutting device of FIG. 2 with a removed portion of the drape 62 adhered to adhesive surface 20 after the application shown in FIG. 5.
Figure 6B:
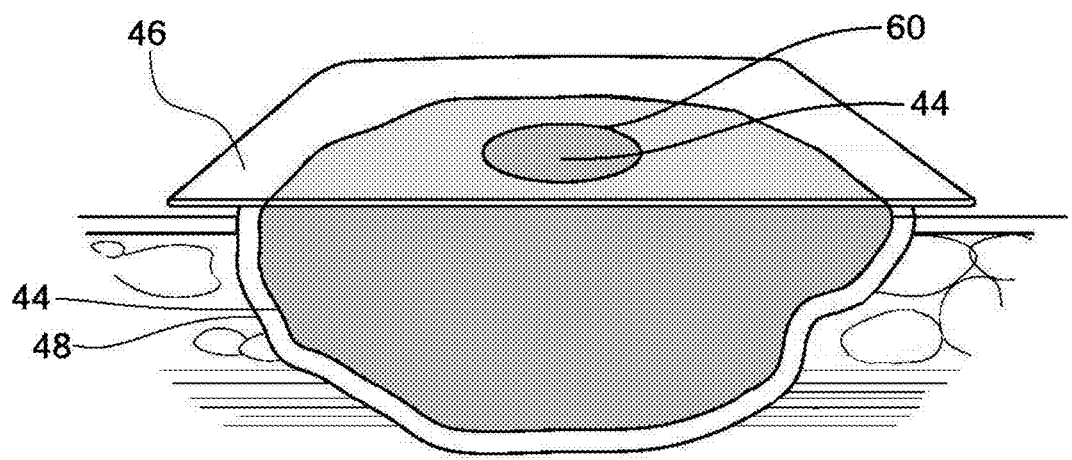
FIG. 6B illustrates the wound site of FIG. 5 after cutting an opening in the drape to expose foam dressing there under.

FIG. 6A illustrates a portion of cut drape 62 adhered to the bottom surface of the cutting tool 10. FIG. 6B illustrates an opening 60 formed in the drape 46 to reveal the foam dressing 44. FIG. 6B shows how the darker grey foam dressing 44 is exposed through the opening 60 in the drape 46. The suction disc 50 can be applied over this opening 60 as shown in FIG. 7.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

The invention claimed is:

1. A method for cutting a wound dressing material disposed on a patient, comprising:
    disposing a cutting tool on the wound dressing material;
    pressing the cutting tool onto the wound dressing material to cause cutting members extending from a bottom surface of a base member of the cutting tool to perforate the wound dressing; and
    lifting the cutting tool away from the patient with a portion of the wound dressing cut by the cutting tool adhered to an adhesive surface disposed on the bottom surface of the base member.

2. The method of claim 1, wherein the cutting members are disposed in a predefined shape and size along the bottom surface thereof.

3. The method of claim 1, wherein the cutting member is a cutting pin.

4. The method of claim 1, wherein the cutting member is a cutting blade.

5. The method of claim 1, wherein the cutting member permanently extend from the bottom surface.

6. The method of claim 1, further comprising covering the bottom surface with a cover during non-use of the cutting tool.

7. The method of claim 1, further comprising pressing downward on a grip of the cutting tool to cause the cutting members to retractably extend from cutting member openings on the bottom surface.

8. The method of claim 7, further comprising retracting the cutting members into the base member via a resilient member when the cutting tool is removed from pressing contact with the wound dressing.

9. The method of claim 1, wherein the cutting members are spaced together to sufficiently perforate the wound dressing to permit separation of a portion of the wound dressing within the cutting members while maintaining the wound dressing external to the cutting members on the patient.

10. The method of claim 1, wherein the wound dressing is a drape used for negative pressure wound therapy.

11. A method for cutting through a drape disposed over a foam dressing for treating a wound by negative pressure wound therapy, the method comprising:
    disposing a cutting tool on the drape;
    pressing the cutting tool onto the drape to cause cutting members extending from a bottom surface of a base member of the cutting tool to perforate the wound dressing without substantially damaging the foam dressing there below or making contact with viable tissue; and
    lifting the cutting tool away from the patient with a portion of the drape cut by the cutting tool adhered to an adhesive surface disposed on the bottom surface of the base member,
    wherein the cutting members are disposed in a predefined shape and size along the bottom surface, the predefined shape and size matching a shape and size proscribed by a system for providing the negative pressure wound therapy.

12. The method of claim 11, wherein the cutting member is a cutting pin.

13. The method of claim 11, wherein the cutting member is a cutting blade.

14. The method of claim 11, wherein the cutting member permanently extend from the bottom surface.

15. The method of claim 11, further comprising pressing downward on a grip of the cutting tool to cause the cutting members to retractably extend from cutting member openings on the bottom surface.

* * * * *